United States Patent [19]
Chaudhari et al.

[11] Patent Number: 5,917,077
[45] Date of Patent: Jun. 29, 1999

[54] METHOD FOR PREPARING DIARYL CARBONATES WITH IMPROVED SELECTIVITY

[75] Inventors: Raghunath Vitthal Chaudhari; Sunil Purushottam Gupte; Ashutosh Anant Kelkar; Subbareddiar Kanagasabapathy; Subramaniam Radhakrishnan, all of Pune, India

[73] Assignee: General Electric Company, Schenectady, N.Y.

[21] Appl. No.: 09/088,023

[22] Filed: Jun. 1, 1998

[51] Int. Cl.⁶ .................................................. C07C 68/00
[52] U.S. Cl. ......................... 558/274; 558/271; 558/272; 558/273
[58] Field of Search ............................................ 558/274

[56] References Cited

U.S. PATENT DOCUMENTS

| | | |
|---|---|---|
| 5,231,210 | 7/1993 | Joyce et al. . |
| 5,284,964 | 2/1994 | Pressman et al. . |
| 5,312,955 | 5/1994 | Pressman . |
| 5,399,734 | 3/1995 | King, Jr. et al. . |

OTHER PUBLICATIONS

U.S. Patent Application Serial No. 08/929,000, filed Sep. 13, 1997, by Eric J. Pressman et al., entitled "Method for Preparing Diaryl Carbonates Employing Hexaalkylguanidinium Halides".

U.S. Patent Application Serial No. 09/040,264, filed Aug. 27, 1997, by Eric J. Pressman et al., entitled "Method for Preparing Diaryl Carbonates Employing Hexaalkylguanidinium Halides".

*Primary Examiner*—Michael G. Ambrose
*Attorney, Agent, or Firm*—Noreen C. Johnson; Douglas E. Stoner

[57] ABSTRACT

Diaryl carbonates such as diphenyl carbonate are prepared by reaction of hydroxyaromatic compounds such as phenol with oxygen and carbon monoxide in the presence of a catalyst composition comprising a Group VIIIB metal such as palladium or a compound thereof, a bromide source such as a quaternary ammonium or hexaalkylguanidinium bromide and a polyaniline in partially oxidized and partially reduced form. The polyaniline is preferably halide-doped and in the form of a blend with a binder polymer containing ether or ester groups and a complex-forming salt.

17 Claims, No Drawings

METHOD FOR PREPARING DIARYL CARBONATES WITH IMPROVED SELECTIVITY

BACKGROUND OF THE INVENTION

This invention relates to the preparation of diaryl carbonates by carbonylation. More particularly, it relates to the employment of a simplified catalyst composition in the carbonylation reaction.

Diaryl carbonates are valuable intermediates for the preparation of polycarbonates by transesterification with bisphenols in the melt. This method of polycarbonate preparation has environmental advantages over methods which employ phosgene, a toxic gas, as a reagent and environmentally detrimental chlorinated aliphatic hydrocarbons such as methylene chloride as solvents.

Various methods for the preparation of diaryl carbonates by a carbonylation reaction of hydroxyaromatic compounds with carbon monoxide and oxygen have been disclosed. In general, the carbonylation reaction has required a rather complex catalyst. Reference is made, for example, to U.S. Pat. No. 5,231,210, 5,284,964 and 5,399,734 and copending, commonly owned application Ser. No. [RD-25582]. The catalyst compositions described therein comprise a Group VIIIB metal (i.e., a metal selected from the group consisting of ruthenium, rhodium, palladium, osmium, iridium and platinum) or a complex thereof. They are used in combination with a bromide source, as illustrated by tetra-n-butylammonium bromide and hexaethylguanidinium bromide.

Other catalytic constituents are necessary in accordance with the above-listed patents and application. They include inorganic cocatalysts, typically complexes of cobalt(II) salts with organic compounds capable of forming complexes, especially pentadentate complexes, therewith. Illustrative organic compounds of this type are nitrogen-heterocyclic compounds including pyridines, bipyridines, terpyridines, quinolines, isoquinolines and biquinolines; aliphatic polyamines such as ethylenediamine and tetraalkylethylenediamines; crown ethers; aromatic or aliphatic amine ethers such as cryptanes; and Schiff bases. The especially preferred inorganic cocatalyst in many instances is a cobalt(II) complex with bis[3-(salicylalamino)propyl]methylamine.

Organic cocatalysts are also necessary. They may include various terpyridine, phenanthroline, quinoline and isoquinoline compounds including 2,2':6',2"-terpyridine, 4-methylthio-2,2':6',2"-terpyridine and 2,2':6',2"-terpyridine N-oxide, 1,10-phenanthroline, 2,4,7,8-tetramethyl-1,10-phenanthroline, 4,7-diphenyl-1,10, phenanthroline and 3,4,7,8-tetramethy-1,10-phenanthroline. The terpyridines and especially 2,2':6',2"-terpyridine have generally been preferred.

It would be desirable to conduct the carbonylation reaction in the presence of a catalyst composition comprising fewer constituents, and especially one which does not require the presence of relatively expensive cobalt complexes and terpyridines. The present invention involves the use of such a catalyst composition.

SUMMARY OF THE INVENTION

The invention is a method for preparing a diaryl carbonate which comprises contacting at least one hydroxyaromatic compound with oxygen and carbon monoxide in the presence of an amount effective for carbonylation of at least one catalyst composition free from metals other than Group VIIIB metals and compounds thereof and free from terpyridines, said catalytic material comprising a Group VIIIB metal or a compound thereof, a bromide source and a polyaniline in partially oxidized and partially reduced form.

DETAILED DESCRIPTION; PREFERRED EMBODIMENTS

Any hydroxyaromatic compound may be employed in the present invention. Monohydroxyaromatic compounds, such as phenol, the cresols, the xylenols and p-cumylphenol, are generally preferred with phenol being most preferred. The invention may, however, also be employed with dihydroxyaromatic compounds such as resorcinol, hydroquinone and 2,2-bis(4-hydroxyphenyl)propane or "bisphenol A", whereupon the products are polycarbonates.

Other essential reagents in the method of this invention are oxygen and carbon monoxide, which react with the phenol to form the desired diaryl carbonate.

An essential constituent of the catalyst composition employed according to the invention is one of the Group VIIIB metals, preferably palladium, or a compound thereof. Thus, palladium black or elemental palladium deposited on carbon are suitable, as well as palladium compounds such as halides, nitrates, carboxylates, salts with aliphatic β-diketones and complexes involving such compounds as carbon monoxide, amines, phosphines and olefins. Preferred in most instances are palladium(II) salts of organic acids, most often $C_{2-6}$ aliphatic carboxylic acids, and of β-diketones such as 2,4-pentanedione. Palladium(II) acetate and palladium(II) 2,4-pentanedionate are generally most preferred.

The catalytic material also contains a bromide source. It may be a quaternary ammonium or quaternary phosphonium bromide or a hexaalkylguanidinium bromide. The guanidinium salts are often preferred; they include the α,ω-bis(pentaalkylguanidinium)alkane salts. Salts in which the alkyl groups contain 2–6 carbon atoms and especially tetra-n-butylammonium bromide and hexaethylguanidinium bromide are particularly preferred.

Another essential catalyst constituent, according to the present invention, is a polyaniline in partially oxidized and partially reduced form. Polyanilines are known in the art. They may be produced by the oxidation of aniline by electrochemical or chemical means.

A typical method of polyaniline preparation is by oxidation of aniline with ammonium persulfate, in an aqueous medium in the presence of a suitable acidic compound such as hydrofluoric or hydrochloric acid. When hydrochloric acid is used, the pH of the aqueous medium is quite low, generally below 1.0. This method is described in an Indian patent application of S. Radhakrishnan and S. Unde, filed in 1997 and entitled "A process for preparation of conducting polyaniline for applications in chemical sensors". It typically affords the polyaniline as a partially oxidized and partially reduced material, with the reduced portion (about 40–60% by weight) comprising —$C_6H_4$NH—structural units and the oxidized portion comprising alternating quinone and phenylene moieties separated by trivalent nitrogen atoms.

One of the characteristics of polyaniline which is important in the present invention is relatively high electrical conductivity. It is often found that the polyanilines prepared by the above-described methods have undesirably low conductivities.

Therefore, it is frequently preferred for the purposes of the invention to employ a halide-doped and especially a chloride-doped polyaniline composition synthesized by a slightly different method including steps of relatively low pH oxidation, blending with an inert binder and complexation. In this method, the aniline is dissolved in an acidic medium, typically aqueous hydrochloric acid, having a pH in the range of about 3.0–4.5 and a suitable oxidizing agent, typically an alkali metal persulfate or ferric chloride with alkali metal persulfate and especially sodium persulfate generally being preferred, is added. Doped polyaniline precipitates upon standing from the resulting reaction mixture. It is separated by conventional means, typically including filtration and drying. It is then blended with a binder polymer containing ether or ester groups; suitable polymers include poly(alkylene oxides) polyphenylene ethers and acrylic ester addition polymers. The resulting polymer mixture is dissolved in a suitable solvent; combined with a salt which forms a complex therewith, such as cupric chloride; and agitated until a thick slurry is obtained. This slurry may be employed as the catalyst constituent.

The preparation of polyaniline compositions useful as catalyst constituents is illustrated by the following examples.

EXAMPLE 1

Aniline, 10 ml, was added dropwise with vigorous stirring to a mixture of 5.5 g of concentrated hydrochloric acid in 150 ml of distilled water to produce a clear liquid having a pH of 4.3. A solution of 5.3 g of ammonium persulfate in 100 ml of water was added slowly, with stirring, and the reaction mixture was allowed to stand for 20 hours at room temperature, whereupon a greenish-brown mass precipitated. The mixture was poured into 1,000 ml of distilled water to precipitate the polyaniline.

The precipitated polyaniline was filtered, washed with distilled water several times and dried. A 200-mg sample thereof was mixed with 800 mg of polyethylene oxide having a molecular weight of about 3,000 and 20 ml of methanol containing 80 mg of cupric chloride. The solution was stirred vigorously until it formed a thick slurry of uniform color and consistency. This slurry was the desired partially reduced, chloride-doped polyaniline.

EXAMPLE 2

Aniline, 9.3 ml, was added dropwise with vigorous stirring to a mixture of 5.5 g of concentrated hydrochloric acid in 150 ml of distilled water to produce a clear liquid having a pH of 3.8. A solution of 3.2 g of ferric chloride in 20 ml of water was added slowly, with stirring, and the reaction mixture was allowed to stand for 24 hours at room temperature, whereupon a greenish mass precipitated. The mixture was poured into 1,000 ml of distilled water to precipitate the polyaniline.

The precipitated polyaniline was filtered, washed with distilled water several times and dried. A 200-mg sample thereof was mixed with 800 mg of polyethylene oxide having a molecular weight of about 3,000 and 20 ml of methanol containing 80 mg of cupric chloride. The solution was stirred vigorously until it formed a thick slurry of uniform color and consistency. This slurry was the desired partially reduced, chloride-doped polyaniline.

The proportion of Group VIIIB metal source employed in the method of this invention is an amount sufficient to provide about 1 gram-atom of metal per 800–10,000 and preferably 2,000–5,000 moles of hydroxyaromatic compound. For each gram-atom of Group VIIIB metal there is usually employed about 5–150, preferably about 20–50, moles of bromide source. Weight ratios of polyaniline to Group VIIIB metal compound are usually in the range of about 0.2–5.0:1.

Gas is supplied to the reaction mixture in proportions of about 2–50 mole percent oxygen, with the balance being carbon monoxide. The gases may be introduced separately or as a mixture, to a total pressure in the range of about 10–250 atmospheres. Reaction temperatures in the range of about 60–150° C. are typical. Drying agents, typically molecular sieves, may be present in the reaction vessel. In order for the reaction to be as rapid as possible, it is preferred to maintain the reaction pressure in accordance with the aforementioned U.S. Pat. No. 5,399,734 until conversion of the hydroxyaromatic compound is complete.

The diaryl carbonates produced by the method of this invention may be isolated by conventional techniques. It is often preferred to form and thermally crack an adduct of the diaryl carbonate with the hydroxyaromatic compound, as described in U.S. Pat. Nos. 5,239,106 and 5,312,955.

The invention is illustrated by the following examples.

EXAMPLES 3–5

High pressure reactors (50 ml capacity) were charged with various reactive batches consisting of approximately 20 g of phenol, 800 mg of tetrabutylammonium bromide and various quantities of palladium(II) acetate and a polyaniline similar to that of Example 1, said polyaniline being in 50% reduced and 50% oxidized form and having a molecular weight of about 3,380. About 4.5 g of freshly activated Type 3A molecular sieves was placed in a basket fixed at the top of each reactor.

The reactors were sealed, flushed twice with carbon monoxide, pressurized with 66.3 atmospheres of carbon monoxide and 5.1 atmospheres of oxygen and heated to 100° C. with vigorous stirring. The progress of the reactions was monitored by recording the pressure drop therein, and the gases were repressurized in a 2:1 ratio of carbon monoxide to oxygen as necessary. When the reaction was complete, the reactor contents were cooled and analyzed. The results are given in the following table. "Phenol conversion" is the proportion of phenol converted to products, and "selectivity"(to diphenyl carbonate) is the amount of diphenyl carbonate produced as a percentage of total reaction products.

|  | Example | | |
| --- | --- | --- | --- |
|  | 3 | 4 | 5 |
| Phenol, g | 20.845 | 21.09 | 19.63 |
| Palladium(II) acetate, mg | 22 | 22 | 44 |
| Polyaniline, mg | 50 | 9 | 10 |
| Molecular sieves, g | 4.56 | 4.0 | 4.0 |
| Reaction time, hrs. | 9 | 8 | 8 |
| Phenol conversion, % | 25 | 13.6 | 47.2 |
| Selectivity, % | 40 | 52 | 6.0 |

What is claimed is:

1. A method for preparing a diaryl carbonate which comprises contacting at least one hydroxyaromatic compound with oxygen and carbon monoxide in the presence of an amount effective for carbonylation of at least one catalyst composition free from metals other than Group VIIIB metals and compounds thereof and free from terpyridines, said catalytic material comprising a Group VIIIB metal or a compound thereof, a bromide source and a polyaniline in partially oxidized and partially reduced form.

2. A method according to claim 1 wherein the hydroxyaromatic compound is phenol.

3. A method according to claim 2 wherein the Group VIIIB metal is palladium.

4. A method according to claim 3 wherein the bromide source is a quaternary ammonium or quaternary phosphonium bromide or a hexaalkylguanidinium bromide.

5. A method according to claim 4 wherein the bromide source is tetra-n-butylammonium bromide or hexaethylguanidinium bromide.

6. A method according to claim 5 wherein the palladium compound is palladium(II) acetate or palladium(II) 2,4-pentanedionate.

7. A method according to claim 4 wherein the polyaniline is in the partially oxidized and partially reduced form with the reduced portion comprising about 40–60% by weight.

8. A method according to claim 7 wherein the polyaniline is halide-doped.

9. A method according to claim 8 wherein the polyaniline is chloride-doped.

10. A method according to claim 8 wherein the polyaniline is prepared by oxidation with alkali metal persulfate or ferric chloride in an aqueous acidic medium having a pH in the range of about 3.0–4.5, blended with a binder polymer containing ether or ester groups and combined with a salt which forms a complex with said polyaniline.

11. A method according to claim 10 wherein the aniline is oxidized with sodium persulfate.

12. A method according to claim 10 wherein the aniline is oxidized with ferric chloride.

13. A method according to claim 10 wherein teh salt is cupric chloride.

14. A method according to claim 4 wherein the proportions of oxygen and carbon monoxide are about 2–50 mole percent oxygen, with the balance being carbon monoxide.

15. A method according to claim 4 wherein the proportion of palladium is about 1 gram-atom per 2,000–5,000 moles of hydroxyaromatic compound.

16. A method according to claim 4 wherein the weight ratio of polyaniline to palladium compound is in the range of about 0.2–5.0:1.

17. A method according to claim 4 wherein about 5–150 moles of bromide source is present for each gram-atom of palladium.

* * * * *